United States Patent
Hu et al.

(10) Patent No.: US 7,297,353 B2
(45) Date of Patent: Nov. 20, 2007

(54) USE OF ANEMONIN FOR TREATING ASEPTIC INFLAMMATIONS

(76) Inventors: Shiqing Hu, 76-2 Datong Road, Guiding Couty 551300 Guizhou (CN); Shixi Hu, 76-2 Datong Road, Guiding County 551300 Guizhou (CN); Qiguo Hu, 76-2 Datong Road, Guiding County 551300 Guizhou (CN)

(*) Notice: Subject to any disclaimer, the term of this patent is extended or adjusted under 35 U.S.C. 154(b) by 0 days.

(21) Appl. No.: 11/272,092

(22) Filed: Nov. 14, 2005

(65) Prior Publication Data

US 2006/0062860 A1    Mar. 23, 2006

Related U.S. Application Data

(63) Continuation-in-part of application No. 10/156,407, filed on May 29, 2002, now abandoned, which is a continuation-in-part of application No. PCT/CN01/00067, filed on Jan. 20, 2001.

(30) Foreign Application Priority Data

Feb. 4, 2000    (CN)    .............................. 00 1 12680

(51) Int. Cl.
*A61K 36/716*    (2006.01)
(52) U.S. Cl. .................................... 424/725
(58) Field of Classification Search .................. None
See application file for complete search history.

(56) References Cited

U.S. PATENT DOCUMENTS 6,071,521 A * 6/2000 Kim ........................... 424/728

FOREIGN PATENT DOCUMENTS

CN        2329301    *    7/1999

OTHER PUBLICATIONS

Asahina (Ber. (1914), vol. 47, pp. 914-916).*
Martin, M.L., et al., "Pharmacologic Effects of Lactones Isolated from Pulsatilla Alpina Subsp. Apiifolia", Journal or Ethnopharmacology, vol. 24, pp. 185-191, (1988).
Cappelletti, E.M., et al., "External Antirheumatic and antineuralgic Herbal Remedies in the Traditional Medicine of North-Eastern Italy", Journal of Ethnopharmacology, vol. 6, pp. 161-190, (1982).

* cited by examiner

*Primary Examiner*—Susan Coe Hoffman
(74) *Attorney, Agent, or Firm*—Gary M. Nath; Tanya E. Harkins; Ari G. Zytcer (57) ABSTRACT

The present invention discloses a medicament useful for treating aseptic inflammations, containing anemonin as an effective ingredient, and use of the anemonin compound in treating aseptic inflammations. The effective ingredient in the present medicament, anemonin, can be extracted and separated from natural plants containing anemonin or its precursor. The present invention also discloses a method for preparing anemonin extract. The present medicament can be formulated into preparations for oral administration, injection and topical application, especially liquid extract, plaster, suppository, liniment, and paint etc., which can be transdermally absorbed.

16 Claims, 1 Drawing Sheet

Figure 1. Graph percutaneous permeation of anemonin.

A, water-saturated solution;   B, 30% ethanol solution.

USE OF ANEMONIN FOR TREATING ASEPTIC INFLAMMATIONS

The present invention is a Continuation-In-Part of U.S. Pat. No. 10/156,407, filed May 29, 2002 now abandoned which is a Continuation-In-Part of International Application No. PCT/CN01/00067 with an international filing date of Jan. 20, 2001, and claims priority to Chinese Patent Application 00112680.6 filed Feb. 4, 2000, the contents of which are incorporated herein by reference in their entirety.

FIELD OF THE INVENTION

The present invention relates to the use of anemonin for treating aseptic inflammations, especially for treating various stubborn pains caused by aseptic inflammations.

BACKGROUND OF THE INVENTION

In the medical field, inflammations can be distinguished into two groups: bacterial inflammations and aseptic inflammations. Bacterial inflammations have widely been taken seriously because they are likely to lead to the attack of acute diseases. Plenty of anti-bacterial drugs such as antibiotics including penicillin and carbapenems have been developed as specific clinical medicaments aimed at bacterial inflammations. While, before this invention, there is no specific, even established effective medicament for aseptic inflammations. That is to say, it is quite a blank for medicaments for specifically treating aseptic inflammations in the international medical field. There isn't any pharmaceutical company which produce specific medicament for aseptic inflammations. Generally, aseptic inflammations include cervical spondylosis, lumbar diseases, periarthritis humeroscapularis, tennis elbow, muscular fascia syndrome, rheumatic arthritis, osteoarthritis, aseptic prostatitis, multiple neuritis, neurodermatitis, tenosynovitis, lumbar muscle strain, ischias, painful heel, migraine, chronic gastritis, early aseptic necrosis of femoral head, bronchial asthma, and other diseases belong to aseptic inflammations as defined in the medical field. Modern medical researches have demonstrated that hyperplastic spurs often stab peripheral soft tissue, then cause inflammatory exudation, edema, accumulation of metabolites and formation of adhesion, which stimulate nerve receptor and cause pain. Degeneration of intervertebral disc, hyperosteogeny, trauma, strain and a series of secondary pathologic variations lead to aseptic inflammations. Edema and adhesion, which is caused by aseptic inflammations around muscle, fascia, ligament, peripheral nerve plexus, joint capsule and vascular wall, compress spinal cord, vertebral artery and nerve root and lead to complex symptoms of cervical and lumbar vertebral which are difficult to be got rid of. Adhesion, calcificated ligament, fascia and myotasis are the main causes of many aseptic inflammatory diseases such as cervical and lumbar vertebral, periarthritis humeroscapulans, muscular fascia syndrome and osteoarthritis, etc. Hundreds millions of people all over the world are suffering from these diseases caused by aseptic inflammations though they are mostly chronic diseases.

SUMMARY OF THE INVENTION

Aiming to the present status that there is no effective medicament for the variety of diseases and stubborn pain caused by aseptic inflammations, in the first aspect, the present invention provides a medicament for treating aseptic inflammations containing anemonin as its effective component. The compound of anemonin can be obtained by chemical synthesis, or especially be prepared from natural materials of Chinese herbs. It is evidenced by clinical tests that a medicament containing this active compound has notable curative effect on stubborn pain and body disorders/diseases, which are caused by aseptic inflammation and are common, frequently encountered and difficult to be cured. Such medicament can eliminate the aseptic inflammations, edema, adhesion caused by aseptic inflammations, and stubborn pain, complex body disorders caused by aseptic inflammation, edema and adhesion. Consequently, it can rapidly cure varieties of aseptic inflammatory diseases with high efficacy and safety. Furthermore, such medicament is non-toxic nor irritant. According to the second aspect of the present invention, the use of the compound of anemonin or the natural abstracts containing anemonin for treating aseptic inflammations is proposed.

This invention also provides a pharmaceutical preparation for treating aseptic inflammations containing anemonin as effective component, especially in topical application forms. It provides the best way of administration for treating aseptic inflammations.

This invention also provides a naturally originated medicament for treating aseptic inflammations containing as effective component the extract liquor of anemonin obtained from Chinese herbal medicine.

Finally, the present invention provides a method for preparing a medicament according to the present invention, especially by extracting and preparing anemonin from natural medical plants. With the method according to the present invention, protoanemonin, which has strong toxicity and side effects, contained in rough material can be turned into non-irritant anemonin, which can then be produced in an industrial scale.

DETAILED DESCRIPTION OF THE INVENTION

The medicament according to the present invention for treating aseptic inflammations comprises a therapeutically effective amount of anemonin. The chemical structural formula of anemonin is as following:

This compound can be prepared from the extracts from any natural Chinese herb containing ranunculin or protoanemonin. Suitable natural Chinese herbs include *Ranunculaceous* plants and *Graminaceous* plants, etc. *Ranunculaceous* plants include: *Ranunculus japonicus* Thunb., *Caltha palustris* L, *Ranunculus sceleratus* L., *Anemone hupehensis* Lem., *Pulsatilla chinensis* (Bge.) Regel, *Anemone raddeana* Regel, *Anemone altaica* Fisch, *Ranunculus Chinensis* Regel, anemonin-containing *Clematis* including *Clematis chinensis* osbeck, *Clematis finetiana* Levi. Et Vant., *Clematis hexapetala* Pall, *Clematis Manshu-*

*rica* Rupr, *Clematis paniculata, Clematis florida, Clematis lasiandra* Maxim, *Clematis uncinata* champ.ex Benth and *Clematis meyeniana* Walp, as well as *Anemone hupehensis* Lem. var. *japonic* (Thunb.) Bowles et Stearn etc. Graminaceous plants include root of *Imperata cylindrica*, ranunculin-containing plants of *Helleborus* (Ranunculaceae), *Anemone* (Anemoneae), *Hepatica* (Anemoneae), *Ranunculus* (Ranunculeae), *Bratrachium* (Ranunculeae), and *Aconitum scaposum* var *vaginatum* (Delphineae).

It is known from the publications prior to the present invention that each of the above natural herbs contains ranunculin or protoanemonin. It has been shown that they have certain anti-tumor activities in clinical tests. It has a long history and a wide use of fresh *Ranunculus japonucus* by topical application. It has good therapeutic effects on many common diseases such as periarthritis humeroscapularis, rheumatic arthritis and ischias. However, protoanemonin is strongly irritant and toxic. Inflammation will be caused if the skin contacts with these plants for a prolonged period, leading to redness, swelling, blistering etc. As a precursor of anemonin, ranunculin is enzymatically cleaved to remove saccharides and turn into protoanemonin. By polymerization, protoanemonin turns into dipolymer anemonin. Some natural herbs per se contain anemonin (mostly are produced during the storage of the herbs). It has been found that anemonin is inhibitory against *staphylococcus, streptococcus, Bacillus diphtheriae, Mycobacterium tuberculosis*, and *E. coli*, etc. Consequently, before this invention, these herbs containing protoanemonin or anemonin were used as antineoplastic, antiseptic and antiphlogistic drugs in clinic. In traditional Chinese medicine, such plants as *Clematis chinensis* are often used to treat rheumatism, promote circulation and relieve pain.

After a long period of study, the present inventor found that whether with oral medication or topical use, the natural Chinese herbs including the above raw herbs containing protoanemonin are all irritant to human body. With oral medication, they result in severe gastro-enteritis and intoxication symptoms such as nausea, vomiting and diarrhea, even stimulate kidney and cause bloody urine and proteinuria. They cause redness, swelling and blister when contacted with skin. But this component has strong antibacterial activity. The above mentioned toxicity and side effects will disappear when water or an organic solvent is added to the raw herbs and the mixture is stored for a prolonged period (optionally with heating), or when ethyl ether, acetone or sulfuric acid is added so as to polymerize two moleculars of protoanemonin into anemonin. The latter compound has specific good effect on treating varieties of stubborn pains and body disorders induced by aseptic inflammations. Especially when a targeting trans-dermal formulation is used on the infected and painful sites, the effects will be very significant. It has been identified that the chemical structure of protoanemonin in raw herbs changes during extraction. That is to say, two molecules of protoanemonin polymerize into non-irritant anemonin. Based on these findings, the present invention proposes a medicament for treating aseptic inflammations containing anemonin as the main active component. Said anemonin can be a product of chemical synthesis, or a extracted product isolated from natural herbs, which is provided in the form of extract liquor of anemonin.

According to the medical classification of inflammations, the aseptic inflammations described in this invention include follow diseases caused by aseptic inflammations: cervical spondylosis, lumbar diseases, periarthritis humeroscapularis, tennis elbow, muscular fascia syndrome, rheumatic arthritis, osteoarthritis, aseptic prostatitis, multiple neuritis, neurodermatitis, tenosynovitis, lumbar muscle strain; ischias, painful heel, migraine, stubborn stomach-ache, cancerous pain, bronchial asthma, and early necrosis of femoral head caused by aseptic inflammations, and other diseases belong to aseptic inflammations as defined in the medical field. It is worthy to note that stubborn chronic rheumatic arthritis, migraine, stubborn stomach-ache, and bronchial asthma can be cured rapidly with topical use of anemonin extract liquor for three times or even just once. This indicates that aseptic inflammation must be one of the causes of rheumatic arthritis, chronic gastritis, migraine and bronchial asthma.

Prior to the present invention, the treatments for these diseases including conventional analgesics or physical therapeutics such as massage, manipulation and traction when the attack of these diseases occurs. Furthermore, the effects of these conventional treatments are temporary. Severe ones need to be treated with operation. Compared to the prior art, an anemonin extract liquor or medicament formulated with anemonin according to the present invention has greatly notable effects on varieties of aseptic inflammatory diseases. Topical application of the medicament may be enough for treating relevant diseases without requiring oral taking of medicine, injection, infusion, operation, acupuncture, massage, manipulation or hospitalization. For example, the relevant diseases can be cured by three times of wet-compressing with anemonin extract liquor. The therapeutic mechanism of the medicament according to the present invention may lay in that: with trans-dermal wet-compressing with anemonin solution on the affected sites, anemonin displays its notable effects of analgesia, anti-inflammation, repercussion, relieving spasm, decomposing adhesion and its strong trans-dermal absorption ability. It can remove in a short time the aseptic inflammations, which have been deposited many years in a muscle, muscle tendon, fascia, joint, synovial bursa, nerve plexus and among vascular walls. It can rapidly remove edema, decompose adhesion, and relieve tendons and calcified ligament. Massive blood enters muscles after the muscles being relaxed, then harmful metabolites such as exudative solution resulted from dilation of blood vessels can be cleared. Once the circulation is improved, the tensile force of a muscle increases. This then relieves even eliminates the pressure onto nerve roots, spinal cord and blood vessels caused by the stimulation and press of aseptic inflammations. Then cervical spondylosis, lumbar diseases, periarthritis humeroscapularis, tennis elbow, muscular fascia syndrome, ischias, painful heel, migraine, stubborn stomach-ache, rheumatic arthritis, lumbar muscle strain, osteoarthritis, aseptic prostatitis, pain due to old injury, tenosynovitis, multiple neuritis, cancerous pain and pain caused by other diseases can be cured. This mechanism is the same as that of treating cervical spondylosis, lumbar diseases, and muscular fascia syndrome with operation to relieve pressure and eliminate stimulation. Swelling pain and dysfunction of movement caused by adhesion and calcification of muscle, fascia and ligament were relieved and turned to normal due to the elimination of aseptic inflammations.

The medicament according to the present invention contains anemonin as the active therapeutic component and optionally suitable pharmaceutically acceptable vehicle or excipient. Whether a vehicle or excipient is used or not and its chose depend on the final dosage form of the medicament. According to conventional pharmaceutical methods, the medicament according to the present invention can be manufactured into preparations suitable for oral administration, injection and topical application. The preparations for topical use include liquid extract, plaster, suppository, liniment, paint, gelata, wet towel and other preparations suitable for the trans-dermal absorption of active components. Anemoninin used in the preparation of the medicament of the present invention may be synthetic, or can be extracted from the mentioned above raw herbs according to previously known methods, e.g., the method as described in Chemistry of Chinese Herbs Components (in Chinese), page 226, published by Science Publishing House (1977). According to this method, preparations for injection, oral or topical use can be prepared with purified anemonin crystal or anemonin extract liquor obtained from ranuculin-containing natural plants (the active component therein is anemonin). Experimental researches have proved that anemonin is of good stability. Anemonin functions as a treatment for varieties of aseptic inflammations without being affected by combination with many Chinese herbs and their chemical components. The stability of anemonin is also shown by the fact that the rapid and effective therapeutic effect of anemonin extract liquor on various aseptic inflammations won't be reduced under unfavorable conditions such as high temperature, low temperature, molding and decaying.

In a preferred embodiment of the present invention, the medicament for treating aseptic inflammations is naturally originated, which comprises, as the active component, an extract liquor obtained by extracting any natural plants or Chinese herbs containing anemonin or its precursors with an organic solvent, water, animal or vegetable oil, brewage vinegar or an inorganic acid.

Therefore, besides the mentioned above methods for preparing the medicament of the present invention, this invention further provides a method for preparing anemonin extract liquor comprising a step of extracting a natural plant or Chinese herbal medicine containing anemonin or its precursor(s) in a sealed container with an organic solvent, water, animal or vegetable oil, brewage vinegar or an inorganic acid. After filtering, clarifying the extracting mixture, the anemonin extract liquor is obtained.

In the method for preparing anemonin extract liquor according to the present invention, cold-maceration or hot-maceration may be made. The starting materials include *Ranunculaceous* plants such as *Ranunculus japonicus* Thunb., *Caltha palustris* L, *Ranunculus sceleratus* L., *Anemone hupehensis* Lem., *Pulsatilla chinensis* (Bge.) Regel, *Anemone raddeana* Regel, *Anemone altaica* Fisch, *Ranunculus Chinensis* Regel, anemonin-containing *Clematis* including *Clematis chinensis* osbeck, *Clematis finetiana* Levi. Et Vant., *Clematis hexapetala* Pall, *Clematis Manshurica* Rupr., *Clematis paniculata, Clematis florida, Clematis lasiandra* Maxim, *Clematis uncinata* champ.ex Benth and *Clematis meyeniana* Walp, as well as *Anemone hupehensis* Lem. var. *japonic* (Thunb.) Bowles et Stearn etc.; and Graminaceous plants such as root of *Imperata cylindrica*, ranunculin-containing plants of *Helleborus* (Ranunculaceae), *Anemone* (Anemoneae), *Hepatica* (Anemoneae), *Ranunculus* (Ranunculeae), *Bratrachium* (Ranunculeae), and *Aconitum scaposum* var. *vaginatum* (Delphineae). Herbal pieces for decoction such as pieces of *Pulsatilla chinensis* (Bge.) Regel, pieces of *Clematis chinensis* osbeck etc. Useful organic solvents include ethanol, methanol, propylene glycol, glycerin, chloroform, or mixture thereof. The cold-maceration used in this invention refers to soaking and extracting the raw material with extracting liquid at room temperature to obtain anemonin extract liquor. Hot-maceration refers to soaking and extracting the raw material in heat extracting liquid to get the extract liquor.

The method of the present invention for preparing anemonin extract liquor is characterized in that it makes protoanemonin contained in raw material turn into anemonin by polymerization and result in anemonin extract liquor having anti-bacterial and anti-inflammation effects, especially anti-aseptic inflammations.

From the practical point of view, a preferred embodiment of the method comprises soaking the raw material at room temperature with 30%-50% ethanol for over 8 months or adding the raw material to the same solvent kept boiling, sealing the container and soaking for over 6 months.

According to the method of the present invention, effective parts of the raw herb can be chosen for extraction, such as the whole grass or a mixture of the whole grass and root of fresh *Ranunculus japonicus* Thunb. After being pulverized, the chosen effective part may be placed into an extraction jar, and an extractant is added in suitable proportion, then the jar is sealed to carry out the extraction. After being extracted, protoanemonin has been polymerized sufficiently and turned into anemonin, and the resultant anemonin has been dissolved in the solvent. After squeezing the contents discharged from the jar and removing the dregs, a juice is obtained. Then the juice may be filtered, and the filtrate is settled. An anemonin extract liquor, a clear yellow transparent liquid, is obtained (the content of anemonin in the extract can be determined with a conventional detection method.

As mentioned above, according to a preferred embodiment of the present invention, a method for converting protoanemonin contained in raw herbs into anemonin is provided, which comprises the step of storing the raw herb and a suitable extractant in suitable amounts under sealing conditions for a prolonged period. The suitable extractants useful in the present invention are the same as described above. Methanol may be hot or cold about 30% strength methanol. Vegetable oil may be castor oil, tea oil or peanut oil. Ethanol, methanol or water is preferably used as the extractant. One herb or any mixture of at least two herbs can be used as the raw herb. For example, the method according to the present invention can be carried out in the so-called hot-extraction manner as follows. The fresh *Ranunculus japonicus* Thunb. whole grass and its root or only the whole grass, after being pulverized, is placed into a container. Hot ethanol in suitable concentration, such as about 40% strength ethanol, used in an amount such that the weight ratio of the fresh *Ranunculus japonicus* Thunb. to ethanol is about 1:1, is then added into the container containing the fresh *Ranunculus japonicus* Thunb. The contents in the container are heated, and then the container is sealed and stored, to polymerize protoanemonin contained in the fresh *Ranunculus japonicus* Thunb. into anemonin and dissolve the resultant anemonin in the solvent. After squeezing the contents discharged from the container and removing the dregs, a juice is obtained. The juice is filtered, and the filtrate is settled. An anemonin extract liquor, a yellow transparent liquid, can be obtained.

Alternatively, the method of the present invention can be carried out in the so-called cold-extraction manner as follows. The fresh *Ranunculus japonicus* Thunb. whole grass and its root or only the whole grass, after being pulverized, is placed into a container. About 40% strength ethanol or about 30% strength methanol, used in an amount such that the weight ratio of the fresh *Ranunculus japonicus* Thunb. to the ethanol is about 1:1, is then added into the container containing the fresh *Ranunculus japonicus* Thunb. Then the container is sealed and stored for a long period, to polymerize protoanemonin contained in the fresh *Ranunculus*

*japonicus* Thunb. into anemonin and dissolve the resultant anemonin in the solvent. After squeezing the contents discharged from the container and removing the dregs, a juice is obtained. Then the juice is filtered, and the filtrate is settled. An anemonin extract liquor, a yellow transparent liquid, is obtained.

Alternatively, the anemonin extract liquor can be obtained by the hot-extraction or cold-extraction method using herbal pieces for decoction as raw material, such as *Clematis chinensis* osbeck herbal pieces or *Pulsatilla chinensis* (Bge.) Regel herbal pieces. More particularly, the raw material is extracted with ethanol in suitable concentration, such as 40% strength ethanol, in such amount that the weight ratio of ethanol to the raw material is about 3:1, according to the hot-extraction or cold-extraction method. The container is sealed and stored for 3 to 6 months while the contents are stirred once a day, to dissolve the anemonin contained in *Clematis chinensis* osbeck or *Pulsatilla chinensis* (Bge.) Regel herbal pieces into ethanol completely. After filtration and settling, a brown anemonin extract liquor is obtained.

If water is used as the solvent, the present method can be carried out in the so-called hot-extraction or cold extraction manner as follows. Water, used in amount such that the weight ratio of the fresh *Ranunculus japonicus* Thunb. to water is about 1:1, and suitable amount of preservative (foodstuff grade) are added directly into a container containing the pulverized fresh *Ranunculus japonicus* Thunb., and the container is sealed and stored, to polymerize protoanemonin contained in the fresh *Ranunculus japonicus* Thunb. into anemonin and dissolve the resultant anemonin in water. After squeezing the contents discharged from the container and removing the dregs, a juice is obtained. The juice is filtered, and the filtrate is settled. An anemonin extract liquor, a yellow transparent liquid, is obtained.

It should be noted, in the present method, a suitable extractant is used to carry out the extraction under specific conditions, the aim is to extract the protoanemonin and anemonin contained in the raw material and to polymerize the extracted protoanemonin into anemonin completely, so as to obtain an anemonin extract liquid, which can be adjusted to desired concentration for therapeutical use or be further processed into suitable preparations. Therefore, the ratio of the extractant to the raw material herb in the present method is not essential.

According to preferred embodiments of the present invention, when the extracted anemonin or anemonin extract liquor is mixed with one or more Chinese herbs or chemical pharmaceuticals, the stability of the anemonin is not affected by the combined Chinese herbs, chemical components contained therein or the pharmaceuticals, and the anemonin can still effectively treat various aseptic inflammations. A stability test for prolonged storage shows, anemonin in the present medication is stable over at least 5 years.

According to preferred embodiments of the present invention, suitable method can be selected with respect to the practical conditions in industry. Either the anemonin compound synthesized in advance or bought in the market, or the anemonin extract obtained by extracting the raw material as described above can be used to further prepare various preparations.

In addition to the extraction methods as described above, percolation, forced-circulation process in extraction jar, supercritical extraction technique, dynamic extraction technique, other separation and extraction techniques useful for herbal effective components, or distillation can also be used.

The present invention also provides a pharmaceutical composition useful for treating aseptic inflammations comprising a therapeutically effective amount of anemonin and a pharmaceutically acceptable vehicle/excipient (if necessary). According to conventional pharmaceutical methods, the composition according to the present invention can be manufactured into preparations suitable for oral administration, injection and topical application. The preparations for topical use include liquid extract, plaster, suppository, liniment, paint and other preparations suitable for the transdermal absorption of active components. For example, said liquid extract can be the anemonin extract liquor obtained by extracting with 30-40% ethanol according to the method of the present invention. This liquid extract can be used to paint the affected sites or be applied to the affected sites with gauze soaked therewith. An anemonin ointment containing ethanol as preservative can be made as follows: 90% ethanol is added to fine powder of fresh *Ranunculus japonicus* at proportion of 1:3 (the fine powder/ethanol) in a container, the mixture is stirred thoroughly and sealed or heated and stored for a prolonged period. During the process, protoanemonin contained in the fresh *Ranunculus japonicus* will be polymerized into anemonin. Herbal pieces of *Clematis chinensis* osbeck or/and of *Pulsatilla chinensis* (Bge.) Regel can be extracted in the same way. The extract liquor may be decocted and concentrated into concentrated herbal granules (suitable additives can be added if necessary). The main active ingredient of such granules is anemonin and can be used for treating aseptic inflammations administered either orally or by topical use.

Clinical use: Anemonin liquid or anemonin extract liquor can be made which contains 12.5 mg anemonin/25 ml of the liquid or solution. In one cycle of treatment for three weeks, 25 ml of the anemonin extract liquor is applied to the affected or painful sites of various aseptic inflammatory diseases with soaked gauze, once per week. The transdermal application may be carried out on an area of about 100 cm$^2$ for about four hours. The curative ratio in one cycle of treatment is as high as 90%. This medicament relieves pain in short time. Notable therapeutic effect can be obtained after the first application. Some patients may be cured with only one application. There's no side effect such as redness, swelling, blistering, running liquid, allergic reaction or pain. This treatment has wide safe window and minimal toxicity. Anemonin liquid or anemonin extract liquor can be prepared into liquid extract, plaster, suppository, liniment, paint and other preparations for topical use. Anemonin can also be formulated into oral tablet, injection, drop pills, oral liquid and medicated wines.

The medicament or pharmaceutical composition according to the present invention can also contain any herbal abstract compatible with anemonin including that from *Mucuna birdwoodiana* Tutcher, *Sargentodoxa cuneata* (Olic.) Rehd. et Wils, *Pittosporum glabratum* Lindl, *Tetrastigma obtectum* Planch, *Lespedeza cuneata* (Dum.Cours.) G.Don, *Helledorus thidetanus* Franch, *Serissa Serissoides* Druce and the like.

It would be appreciated that the present invention is based on finding and providing the use of anemonin or medicament containing anemonin in treating aseptic inflammations. Additionally, protoanemonin contained in raw herbs is effectively polymerized into anemonin according to the method of the present invention. Because of this inversion from protoanemonin to anemonin, the irritant effect of protoanemonin to the body, especially to skin is eliminated. The medicament can effectively treat various aseptic inflammatory diseases or various stubborn pains caused by aseptic inflammations by topical application on the body. It has notable effects on cervical spondylosis, lumbar diseases, periarthritis humeroscapularis, rheumatic arthritis, ischias, pain due to old injury, aseptic prostatitis, bronchial asthma, stubborn stomach-ache and cholecystitis. With the application of medicament containing anemonin, aseptic inflammations can be effectively treated. The clinical tests indicated that the medicament of this invention has a notable therapeutic effect on aseptic inflammations and is effective in over 85% cases. It does have the effect of clearing away toxic agents from the body, relieving rigidity of muscles and activating collaterals, relieving swelling and pain from the point of view of traditional Chinese medicine.

Acute toxicity test and toxicity test in prolonged term have been done with the active anemonin extract liquor. The results are as follows.

By intraperitoneal administration, the maximal tolerating dose for guinea pig was 266 g/kg without any intoxication or death. By topical administration, no intoxication or death was observed when the area of administration reached 10% of animal's body surface area. By successive topical administrations for 4 weeks, no abnormal or pathologic change was observed on the weight, visceral coefficient, hemogram, liver function, kidney function, internal organs and skin of the tested guinea pigs.

The results of animal tests also show that the medicament of the present invention is non-irritant and non-allergenic, especially for skin. It won't cause pathologic change to injured skin by repeated use. So it will not hamper the skin wound from healing.

Specific embodiments and efficacy of the present invention will be further illustrated with reference to the following Examples. The protection scope for the present invention is defined in the claims. Any variation based on the spirit of the present invention such as polymerizing protoanemonin into anemonin with any other feasible method and employing other forms of medicament containing anemonin or similar ingredient as the treatment of aseptic inflammations shall fall into the scope of this invention.

EXAMPLES

Example 1

The fresh *Ranunculus japonicus* Thunb. whole grass and its root or only the whole grass picked in April to September, after being pulverized, was used as raw material. 50 kg of the raw material was placed into a ceramic or plastic container. Fifty kg of 40% strength ethanol was heated to its boiling point, and then was added into the container containing the fresh *Ranunculus japonicus* Thunb. The contents in the container were heated to boiling, and then the container was sealed and stored for a half year or more, to polymerize protoanemonin contained in the fresh *Ranunculus japonicus* Thunb. into anemonin and dissolve the resultant anemonin in the solvent. After squeezing the contents discharged from the container and removing the dregs, a juice was obtained. Then juice was filtered, and the filtrate was settled. An anemonin extract liquor, a yellow transparent liquid, was obtained. Determined with a conventional detection method, the content of anemonin in the effective ingredients of the extract was about 90%. The extract was then adjusted with ethanol to from a preparation containing 12.5 mg anemonin per 25 ml liquor. The preparation was for topical use.

Alternatively, the anemonin extract can be obtained by cold-extraction for one year or more with ethanol.

Example 2

Using either the whole grass or the root or a mixture thereof of *Ranunculus* plants selected from the group consisting of: fresh *Ranunculus japonicus* Thunb., *Caltha palustris* L., *Ranunculus sceleratus* L., *Anemone hupehensis* Lem., *Pulsatilla chinensis* (Bge.) Regel, nine kinds of *Clematis* and root of *Imperata cylindrical, Anemone raddeana* Regel, *Ranunculus Chinensis* Regel, *Anemone altaica* Fisch and *Anemone hupehensis* Lem. var. *japonic* (Thunb.), an anemonin extract was obtained by hot-extraction or cold-extraction with ethanol, and a preparation suitable for topical application or a liniment was obtained according to the method of Example 1 (dried plants of the herbs can alternatively be used as the raw material).

Example 3

*Clematis chinensis* osbeck herbal pieces, or a mixture of *Clematis chinensis* osbeck herbal pieces and *Pulsatilla chinensis* (Bge.) Regel herbal pieces was used as raw material. The raw material was placed in a container. 40% strength ethanol, in such amount that the weight ratio of ethanol to the herbal pieces is 3:1, was heated to its boiling point, and then was added into the container. The contents in the container were heated to boiling, and then the container was sealed and stored for 3 months while the contents were stirred once a day, to dissolve the anemonin contained in *Clematis chinensis* osbeck and/or *Pulsatilla chinensis* (Bge.) Regel herbal pieces into ethanol completely. After filtration and settling, a brown anemonin extract liquor was obtained, which can be concentrated, refined and granulated to from a granule preparation.

Example 4

Using the cold-extraction method, 100 kg of *Clematis chinensis* osbeck herbal pieces, as raw material, was extracted with 300 kg of 40% strength ethanol at room temperature for six months, while the contents in the container were stirred once a day, to dissolve the anemonin contained in *Clematis chinensis* osbeck herbal pieces into ethanol completely. After filtration and settling, a brown anemonin extract was obtained, which can be concentrated, refined and granulated to from a granule preparation.

Alternatively, a mixture of *Clematis chinensis* osbeck and *Pulsatilla chinensis* (Bge.) Regel herbal pieces can be used as the raw material to replace *Clematis chinensis* osbeck herbal pieces.

Example 5

Using the hot-extraction or cold-extraction method, 100 kg of water and 50 g of sodium benzoate as preservative were added into a container containing 100 kg of pulverized fresh *Ranunculus japonicus* Thunb., and the container was sealed and stored 8 to 12 months or more, to polymerize protoanemonin contained in the fresh *Ranunculus japonicus* Thunb. into anemonin and dissolve the resultant anemonin in water. After squeezing the contents discharged from the container and removing the dregs, a juice was obtained. The juice was filtered, and the filtrate was settled. An anemonin extract liquor, a yellow transparent liquid, was obtained, which can be used in the next steps for preparing preparations.

Example 6

30 kg of 95% strength ethanol as preservative and solvent was added into a container containing 100 kg of pulverized fresh *Ranunculus japonicus* Thunb., and contents were stirred thoroughly to from a homogeneous mixture. The container was sealed and stored at room temperature or an elevated temperature for 8 to 12 months or more, to polymerize protoanemonin contained in the fresh *Ranunculus japonicus* Thunb. into anemonin and dissolve the resultant anemonin in ethanol. Depending upon the consistency of the resultant extract, a proper amount of vaseline was added and stirred uniformly to obtain an anemonin ointment.

Example 7

Following the method described in Chemistry of Chinese Herbs Components, page 226 (published by Science Publisher, 1977), *Pulsatilla chinensis* (Bge.) Regel whole grass as raw material was steam distillated. The resultant distillate was extracted with diethyl ether, after further treatment with ethanol, the anemonin crystal was obtained (which is also market available), which can be used further to prepare preparations for topical application, oral administration, injection, or suppository or liniment, etc.

Example 8

A liquor which contains about 12.5 mg anemonin per 25 ml liquor was prepared with the anemonin extract obtained in Example 1, and 100 cm² wet towels were prepared by soaking non-woven fabrics with the liquor.

Example 9

Anemonin powder was added into lanoline and mixed thoroughly to form an ointment, which contains 12.5 mg anemonin per 25 ml. The ointment is for topical application, which is applied on skin for 5-6 hours per dosage.

Pharmacodynamics Tests

A. The Following Tests were Carried out Using the Topical Preparation of Example 1 (Commercial Name Guanvin Dew):

1. Analgesic Test with Formalin

The experiment included 5 groups of mice totaling 80 and each weighed 18-22 g: high concentration group, moderate concentration group, low concentration group (Guanyin Dew was administered at 12.5 mg/25 ml, 8.75 mg/25 ml, and 6.25 mg/25 ml respectively), dolantin group (25 mg/kg) and control group (same volume of 25% ethanol). Dolantin was intraperitoneal injected and other groups received test medication on left and right hind feet. 15 minutes after administration, 0.03 ml of 2.5% formalin was given to each mouse by subcutaneous injection on right hind foot and then the test medication was applied again. Then, the number of times of each mouse's licking its right hind foot in 15 minutes was counted.

Results: high concentration of Guanyin Dew has significant analgesic effect on pain induced by formalin. The number of times of mice's licking their right hind feet decreased notably compared with the control group with $p<0.05$ (see Table A-1).

TABLE A-1

Inhibiting effect of Guanyin Dew on mice's licking foot

| Groups | Animal number | Times of licking hind feet | Value of P | Rate of inhibition(%) |
|---|---|---|---|---|
| Control | 16 | 15.68 ± 4.13 | | |
| High | 16 | 9.13 ± 6.20 | <0.05 | 42 |
| Moderate | 16 | 12.44 ± 7.20 | >0.05 | 21 |
| Low | 16 | 13.79 ± 5.33 | >0.05 | 12 |
| Dolantin | 16 | 0.00 ± 0.00 | <0.001 | 100 |

2. Analgesic Test with Hot Plate

This experiment included 4 groups of female mice, totaling 64 and each weighed 18-22 g, selected for normal pain reaction with 55° C. hot plate: high concentration group, low concentration group, dolantin group and control group. The route of administration and dosage are the same as described in the test with formalin. Dolantin was intraperitoneal injected and other groups received test medication on left and right hind feet and abdomen. 30, 60 and 90 minutes after the administration, the mice were put on a 55° C. hot plate and the latent time of each mouse for pain reaction was determined.

Results: high concentration of Guanyin Dew has significant analgesic effect on pain induced by hot plate. The latent time of mice for pain reaction prolongs notably and the pain threshold increases remarkably compared with the control group with $p<0.05$ (see Tables A-2 and A-3).

TABLE A-2

Effect of Guanyin Dew on the latent time for pain reaction $\bar{X}(\pm SD)$

| | | Latent time for pain reaction (second) | | | |
|---|---|---|---|---|---|
| Groups | No. | Before administration | 30 min after administration | 60 min after administration | 90 min after administration |
| Control | 16 | 29.33 ± 4.12 | 30.13 ± 5.19 | 29.69 ± 7.33 | 29.21 ± 8.18 |
| High | 16 | 28.46 ± 3.49 | 31.33 ± 7.21 | 45.49 ± 9.47 | 47.34 ± 10.29 |
| P | | | >0.05 | <0.05 | <0.05 |
| Low | 16 | 30.12 ± 5.03 | 31.78 ± 6.32 | 35.26 ± 7.79 | 36.30 ± 9.74 |
| P | | | >0.05 | >0.05 | >0.05 |
| Dolantin | 16 | 30.08 ± 4.92 | 49.86 ± 5.23 | 54.29 ± 9.27 | 58.31 ± 11.23 |
| P | | | <0.01 | <0.001 | <0.001 |

TABLE A-3

Effect of Guanyin Dew on pain threshold

| | | Increase of pain threshold (%) | | |
|---|---|---|---|---|
| Groups | Number of animals | 30 min after administration | 60 min after administration | 90 min after administration |
| Control | 16 | 3 | 1 | 0 |
| High | 16 | 10 | 60 | 66 |
| Low | 16 | 6 | 17 | 21 |
| Dolantin | 16 | 66 | 80 | 94 |

3. Anti-Swelling Test on Rat's Hind Foot

This experiment included 4 groups of rats totaling 40 and each weighed 200-250 g: high concentration group, low concentration group (12.5 mg/25 ml, 6.25 mg/25 ml respectively), fluocinolone acetonide group, control group (the same volume of 25% ethanol). Fluocinolone acetonide was given using a 0.025% ointment, and other groups received corresponding medicament on the left and right hind feet prior to subcutaneous injection of 0.1 ml of 1% carrageenan on the metatarsus of each rat's right hind foot. Immediately after the administration of carrageenan, corresponding medicament was applied on the right hind foot. The metatarsal perimeters of right and left hind foot of each rat were measured 2, 3, 4, and 5 hours after the final administration. The difference between the metatarsal perimeters of the two feet of each rat is taken as a measure of swelling. Corresponding medicament was applied again on rat's right hind foot after each measurement.

Results: high concentration of Guanyin Dew has significant inhibiting effect on the swelling of rat's hind foot in the test compared with the control group with $p<0.05$. See Table A-4.

TABLE A-4

Inhibiting effect of Guanyin Dew on swelling of rat's hind foot ($\overline{X} \pm SD$)

| | | Degree of tumefaction (cm) | | | |
|---|---|---|---|---|---|
| Groups | No. | 2 hours | 3 hours | 4 hours | 5 hours |
| Control | 10 | 1.44 ± 0.21 | 1.48 ± 0.13 | 1.47 ± 0.19 | 1.45 ± 0.13 |
| High | 10 | 1.24 ± 0.23 | 1.01 ± 0.17 | 0.97 ± 0.21 | 0.92 ± 0.18 |
| P | | >0.05 | <0.05 | <0.05 | <0.05 |
| Low | 10 | 1.37 ± 0.19 | 1.36 ± 0.21 | 1.39 ± 0.24 | 1.40 ± 0.14 |
| P | | >0.05 | >0.05 | >0.05 | >0.05 |
| Fluocinolone acetonide | 10 | 0.91 ± 0.20 | 0.92 ± 0.13 | 0.90 ± 0.18 | 0.92 ± 0.24 |
| P | | <0.01 | <0.01 | <0.01 | <0.01 |

4. Test on Isolated Ileum of Guinea Pig

Four guinea pigs, weighed each 300-350 g, 2 male and 2 female, were used in this experiment. Ileum was taken out and put into cold Tyode's solution bubbled with oxygen immediately after the animal was sacrificed. The isolated ileum was cleaned and cut into segments of 2-2.5 cm. Both ends of two intestinal segments were ligated. One end of the segment was tied on an aeration hook and put into a thermo-constant Magnus's bath. The other end of the segment was connected to a tension transducer connected with a recorder. The contraction and relaxation of the ileum were recorded after the addition of Guanyin Dew, acetylcholine ($10^{-9}$) and atropine (0.05%).

Results: high concentration of Guanyin Dew significantly relaxes myenteron stimulated by acetylcholine.

B. Effect of Anemonin on Functions of T-Lymphocytes and B-Lymphocytes 1.0 Abstract Anemonin is the main effective ingredient of HUSAN-TIE, which, externally applied, can diminish inflammations and relieve pains. To investigate the action mechanism of inflammation diminishment of anemonin, we firstly examined the effects of HUSANTIE on functions of T-1's and B-1's, which are the main responsive cell to inflammations in the immuno-system of body. In the experiments of mitogen-induced responsive proliferation of T-1's and B-1's, anemonin exhibited remarkable immunosuppressed effect (anti-inflammation action) on responsive proliferation of T-1's and B-1's and obvious inhibition effect on livability of lymphocytes in vitro system by killing the lymphocytes directly.

2.0. Aim

In the inflammatory tissues, there are always inflammatory lymphocyte soakage, inflammatory factor secretion, injury or pain symptoms induced by bacterial inflammations or aseptic inflammations, and these symptoms are the basic forms of pathological response.

The applicant investigated the anti-inflammation mechanism of anemonin, the main effective ingredient of HUSAN-TIE (a wet towel mentioned in example 8), from points of view of pathological and immunological researches. Using in vitro system, the effects of HUSANTIE on functions of normal lymphocytes by the mitogen-induced responsive proliferation of T-1's and B-1's method were examined firstly. If responsive proliferation was elevated by medicament, that is to say, the immunocompetence was enhanced, HUSANTIE would function in promotion of inflammatory response. If responsive proliferation was inhibited, that is to say, the immunocompetence was reduced, HUSANTIE would be supposed to bear anti-inflammation activity. A close relation of a result to its cause exists physiologically and pathologically between inflammation and pain as well as anti-inflammation action and alleviation of pain. This makes it possible that the medicament with immuno-suppression activity can be used to relieve pains induced by various inflammations in kinds of tissues such as arthritis, rheumatic arthritis etc. Examining the effect of anemonin on the function of lymphopoiesis of T-1's and B-1's will facilitate pharmacologic action mechanism of anti-inflammation and acesodyne to be realized.

3.0. Materials 3.1 Animals

ICR mice (Shanghai Center of Experimental Animal, Chinese academy of Sciences), which were male and 6 to 8 weeks old, were used in this experiment. The certificate number of the mice is No. 99-003 (Shanghai Experimental Animal Center, Chinese Academy of Science). The mice were raised in a animal room (specific pathogen free, SPF) in Shanghai Institute of Material medical, Chinese academy of Sciences, with 12 hr/12 hr light/dark of photoperiod, 24° C. of room temperature and 50% to 60% of relative humidity.

3.2 Reagents

MTT (3-(4,5-dimethylthiazol-2-yl)-2,5-diphenyltetrazoli-umbromide), ConA (Conannavalin A) and LPS (Lipopolysacchride from *Escherichia coli* Serotype 055:B5) were purchased from Sigma Chemical Co.).

[³H] thymidine was the product of Shanghai Atomic Energy Institute.

RPMI-1640 culture solution containing 10% inactivated Fetal Bovine was the product prepared by GIBCO, Other reagents are analytical pure and produced in China, including HEPES buffer (10 mM), Penicillin (100 IU/ml), streptomycin (100 µg/ml), glutamine (2 mM), and α-mercaptopurine (50 uM, pH 7.2).

4.0. Dosages

The highest concentration of anemonin used in the experiment was 100 µg/ml, and the anemonin was diluted by 10 times into six levels of final concentration: 10 µg/ml, 1 µg/ml, 0.1 µg/ml, 0.01 µg/ml, and 0.001 µg/ml.

5.0. Methods 5.1 Effect of the Medicament on Survival Rate of Lymphocytes 5.1.1. Mice were sacrificed by removing spondyle, spleen was cut off and then ground to obtain single cell suspension. After erythrocytes were got rid of the remained cells were diluted to $4 \times 10^6$ ml with RPMI-1640 culture solution containing 10% fetal bovine serum. In addition, all these performances must be sterile.

5.1.2. 200 µl solution in total volume (including 100 µl the cell suspension, 50 µl sample and 50 µl culture solution containing 10% fetal bovine serum) was dispensed on 96-well plate. 100 µl the cell suspension and 100 µl culture solution (200 µl in total volume) were added as negative control.

5.1.3. The cell was cultured at 37° C. and under 5% $CO_2$ in incubator for 48 hours, and added MTT to the plate at 2011/well 6 to 7 hours before the end of culture.

5.1.4. 100 µl of supernatant was sucked out when the culture was ended, and then lytic solution was added at 100 µl/well. The plates were kept in incubator for 6 to 7 hours. The survival rate was calculated according to the OD value (at 570 nm) measured by microplate reader.

5.2. Effect of the Medicament on Responsive Proliferation of Lymphocytes 5.2.1. Mice were sacrificed by removing spondyle, spleen was cut off in a sterile condition and then ground to obtain single cell suspension. After erythrocytes were got rid of the remained cells were diluted to $4 \times 10^6$ ml with RPMI-1640 culture solution containing 10% fetal bovine serum.

5.2.2. 200 µl solution in total volume (including 100 µl the cell suspension, 50 µl sample and 50 µl ConA or LPS) was dispensed on 96-well plate.

50 µl culture solution containing 10% fetal bovine serum, instead of 50 µl sample, was added as negative control, in which the total volume was also 200 µl.

5.2.3. The cell was cultured at 37° C. and under 5% $CO_2$ in incubator for 48 hours, and [³H] thymidine ($1.9 \times 10^4$ Bq) was added to the plate at 25 µl/well 12 hours before the end of culture.

5.2.4. The culture was continued. The plates were then stored at −20° C. in refrigeratory after the culture. The thawed cells were collected to fiberglass membrane (Nitrocellose membrane) with cell collector when detecting. After the addition of Scintillation solution, the quantity of [³H] thymidine incorporated into DNA of cells was detected by Beta counter (MicroBeta Trilux, PerkinElmer LifeSciences). The proliferation of lymphocytes was indicated by cpm value.

6.0. Results and Conclusions

The experiment was repeated twice, and the results of each were identical.

6.1 Effect of the Medicament on Survival Rate of Lymphocytes

Effect of different concentrations of Anemonin on survival rate of lymphocytes were determined, said lymphocytes were from the whole spleen of ICR mice after 48-hour culture.

TABLE B-1

| Sample | Concentration µg/ml | MTT Average of OD values | SD | P value | Decrease of survival rate of lymphocytes Yes/No |
|---|---|---|---|---|---|
| Negative control | 0 | 0.153 | 0.002 | | |
| Anemonin | 1 | 0.052 | 0.005 | 0.0003 | Yes |
| Anemonin | 10 | 0.002 | 0.022 | 0.0069 | Yes |
| Anemonin | 100 | 0.163 | 0.007 | 0.1448 | |

TABLE B-2

| Sample | Concentration µg/ml | MTT Average of OD values | SD | P value | Decrease of survival rate of lymphocytes Yes/No |
|---|---|---|---|---|---|
| Negative control | 0 | 0.110 | 0.009 | | |
| Anemonin | 0.001 | 0.087 | 0.009 | 0.0322 | Yes |
| Anemonin | 0.01 | 0.068 | 0.012 | 0.0096 | Yes |
| Anemonin | 0.1 | 0.061 | 0.006 | 0.0028 | Yes |
| Anemonin | 1 | 0.002 | 0.003 | 0.0010 | Yes |
| Anemonin | 10 | 0.008 | 0.004 | 0.0006 | Yes |
| Anemonin | 100 | 0.145 | 0.009 | 0.0089 | |

In the results above, it was found that Anemonin obviously inhibited the survival rate of lymphocytes from the whole spleen of mice, and exhibited direct killing action of the lymphocytes. Anemonin in a final concentration range from 0.001 µg/ml to 10 µg/ml exhibited obvious inhibition in survival rate of the lymphocytes (Table B-1 and B-2).

6.2 Effect of the Medicament on ConA-Induced Responsive Proliferation of T-Lymphocytes Effect of the medicament on ConA-induced responsive proliferation of T-lymphocytes was examined, said T-lymphocytes were from the whole spleen of mice. ConA at 51 µg/ml final concentration was used as the stimulator to induce responsive proliferation of T-lymphocytes from the whole spleen of ICR homogenous mice (cultured in vitro for 48 hours).

TABLE B-3

| Sample | Concentration of T-lymphocytes ConA stimulation µg/ml | Average of CPM values | SD | Proliferation of T-lymphocytes General assess of activity Enhancement/Inhibition |
|---|---|---|---|---|
| Negative control | | 2126 | 431 | |
| Positive control | | 16408 | 632 | |
| Anemonin | 1 | 8650 | 848 | −47% |

TABLE B-3-continued

| Sample | Concentration of T-lymphocytes ConA stimulation | | | Proliferation of T-lymphocytes General assess |
|---|---|---|---|---|
| | μg/ml | Average of CPM values | SD | of activity Enhancement/Inhibition |
| Anemonin | 10 | 171 | 16 | −99% |
| Anemonin | 100 | 160 | 18 | −99% |

TABLE B-4

| Sample | Concentration of T-lymphocytes ConA stimulation | | | Proliferation of T-lymphocytes General assess |
|---|---|---|---|---|
| | μg/ml | Average of CPM values | SD | of activity Enhancement/Inhibition |
| Negative control | | 2281 | 188 | |
| Positive control | | 17471 | 358 | |
| Anemonin | 0.001 | 15466 | 501 | −11% |
| Anemonin | 0.01 | 19386 | 653 | 11% |
| Anemonin | 0.1 | 15284 | 1539 | −13% |
| Anemonin | 1 | 8438 | 204 | −52% |
| Anemonin | 10 | 46 | 20 | −100% |
| Anemonin | 100 | 155 | 232 | −99% |

The results showed Anemonin in a final concentration range from 0.1 μg/ml to 100 μg/ml remarkably inhibited ConA-induced responsive proliferation of lymphocytes from mice (Table B-3 and B-4).

6.3 Effect of the Medicament on LPS-Induced Responsive Proliferation of B-Lymphocytes Effect of the medicament on LPS-induced responsive proliferation of B-lymphocytes was examined, said B-lymphocytes were from the whole spleen of mice. LPS at 10 μg/ml final concentration was used as the stimulator to induce responsive proliferation of B-lymphocytes from the whole spleen of ICR homogenous mice (cultured in vitro for 48 hours).

TABLE B-5

| Sample | Concentration of B-lymphocytes LPS stimulation | | | Proliferation of B-lymphocytes General assess |
|---|---|---|---|---|
| | μg/ml | Average of CPM values | SD | of activity Enhancement/Inhibition |
| Negative control | | 3214 | 144 | |
| Positive control | | 15230 | 845 | |
| Anemonin | 1 | 10137 | 342 | −33% |
| Anemonin | 10 | 190 | 49 | −99% |
| Anemonin | 100 | 164 | 12 | −99% |

TABLE B-6

| Sample | Concentration of B-lymphocytes LPS stimulation | | | Proliferation of B-lymphoctes General assess |
|---|---|---|---|---|
| | μg/ml | Average of CPM values | SD | of activity Enhancement/Inhibition |
| Negative control | | 4389 | 438 | |
| Positive control | | 36753 | 507 | |
| Anemonin | 0.001 | 39272 | 3839 | 7% |
| Anemonin | 0.01 | 39551 | 2461 | 8% |
| Anemonin | 0.1 | 39615 | 4654 | 8% |
| Anemonin | 1 | 32154 | 2629 | −13% |
| Anemonin | 10 | 40840 | 3712 | 11% |
| Anemonin | 100 | 24523 | 646 | −33% |

The results showed that anemonin in a final concentration range from 1 μg/ml to 100 μg/ml remarkably inhibited LPS-induced responsive proliferation of B-lymphocytes from mice (Table B-5 and B-6).

7.0 Discussion 7.1.1 Anemonin reduced the liability of all the T-1's and B-1's of rat's spleen by killing directly lymphocytes, and 0.001~10 ug/ml of Anemonin exhibited obvious effect on reduction of the liability.

7.1.2 0.1~100 ug/ml of Anemonin sharply inhibited ConA-induced proliferation of rat's T-1's.

7.1.3 1~100 ug/ml of Anemonin sharply inhibited LPS-induced lymphopoiesis of rat's B-1's.

7.2 Combined the related symptoms and curative effects provided by sample consignor, the curative function of Anemonin, the main effective ingredient of HUSANTIE (a wet towel), was confirmed in the treating tissue pains and dysfunction induced by various aseptic inflammations. The results above implied that Anemonin can be absorbed percsutaneously when HUSANTIE (a wet towel) is used in treating aseptic inflammations such as cervical spondylosis, thereby affects inflammatory lymphocyte's function, reduces its activity, inhibits the inflammatory response, consequently diminishes inflammations and relieves pains.

C. Anti-Inflammatory Test 1.1 Materials 1.1.1 Animals

Male and female Kunming strain mice (24-28 g), Male and female ICR strain mice (26-30 g), and male Wistar rats (160-180 g) were obtained from Shanghai Experimental Animal Center, Chinese Academy of Sciences (Grade II, Certificate No 99-003). The animals were maintained in an environment with controlled temperature. Food and water were provided ad libitum.

1.1.2 Reagents

Anemonin was provided by Guizhou Huding HUSANTIE Pharmaceutical Limited Company. The liniment solutions of anemonin were prepared by dissolving different concentrations of anemonin in 25% heated ethanol for in vivo experiments, and anemonin dissolved in dimethyl sulfoxide fot in vitro use. Carregeenan, Conannavalin A (Con A) and Lipopolysacchride (LPS) wee purchased from Sigma Chemical Co. [$^3$H] Thymidine was produced by Shanghai Institute of Atomic Energy. Fluocinoloni Acetonidi Acetas (FAA) was provided by the Ninth Pharmary Company of Shanghai. Other chemicals were reagent grade.

1.1.3 Statistical Analysis

Data were presented as mean±SD. The data were evaluated by Student's T-test P<0.05 was considered to be statistically significant.

ethanol). The paw volumes of rats were measured at 0, 2 h, 3 h, 4 h, 5 h, 6 h after injection of carrageenan. The paw edema was represented by subtracting the volume of the untreated same paw from that of the treated paw. Table C-2 shows that this compound significantly reduced paw edema development in a dose-dependent manner. The steroidal anti-inflammatory drug FAA also significantly inhibited edema formation.

TABLE C-2

Effect of external anemonin on carrageenan-induced paw edema in rat

| Compounds | animals | Paw edema (ml) | | | | |
|---|---|---|---|---|---|---|
| | | 2 h | 3 h | 4 h | 5 h | 6 h |
| 25% ethanol | 8 | 0.28 ± 0.10 | 0.32 ± 0.11 | 0.42 ± 0.13 | 0.44 ± 0.13 | 0.47 ± 0.19 |
| anemonin 2 mg/ml | 8 | 0.25 ± 0.08 | 0.16 ± 0.08* | 0.25 ± 0.07** | 0.30 ± 0.06 | 0.31 ± 0.10* |
| anemonin 0.5 mg/ml | 8 | 0.24 ± 0.13 | 0.21 ± 0.08* | 0.25 ± 0.07* | 0.35 ± 0.10 | 0.40 ± 0.08 |
| Anemonin 0.125 mg/ml | 8 | 0.24 ± 0.06 | 0.20 ± 0.09 | 0.33 ± 0.08 | 0.36 ± 0.11 | 0.39 ± 0.08 |
| FAA | 8 | 0.13 ± 0.05** | 0.09 ± 0.07*** | 0.11 ± 0.08*** | 0.09 ± 0.07** | 0.09 ± 0.11*** |

*$P < 0.05$;
**$P < 0.01$;
***$P < 0.001$, compared to 25% ethanol (Student's T-test)

2.2 Methods and Results 2.2.1 Effect of External Anemonin on Acute Ear Edema of Mice Induced by Dimethylbenene The mice were randomly divided into 5 groups. Thirty minutes and sixty minutes after applying dimethylbenene (50 μl) to the anterior and posterior surfaces of the right ear, 25% ethanol (50 μl), the linimene solutions of anemonin (0.05, 0.5, 5 mg/ml, 50 μl) and FAA (a positive control) were applied on the same ears of mice respectively. The left ear was considered as control. Two hours after dimethylbenene application, mice were killed and both ears were removed. Circular sections were taken, using a 9 mm-diameter borer, and weighed. The increase in weight caused by the irritant was measured by subtracting the weight of the untreated left ear section from that of the treated right ear section. As shown in Table C-1, in the dimethylbenene-induced ear edema model, when anemonin (0.05-5 mg/ml) was applied, ear edema formation was inhibited in a dose-dependent manner. The inhibitory effect of this compound at doses of 2.5-25 μg/ear was statistically significant.

TABLE C-1

Effect of external anemonin on dimethylbenene-induced ear swelling in mice

| Compounds | Animals | Ear swellin (mg) |
|---|---|---|
| 25% ethanol | 10 | 24 ± 6 |
| anemonin 5 mg/ml | 10 | 12 ± 4*** |
| anemonin 0.5 mg/ml | 10 | 16 ± 4** |
| anemonin 0.05 mg/ml | 10 | 18 ± 7 |
| FAA | 10 | 10 ± 1.8*** |

**$P < 0.01$;
***$P < 0.001$, compared to 25% ethanol (Student's T-test)

2.2.2 Effect of External Anemonin on Acute Hind Paw Edema of Rats Induced by Carrageenan The animals were injected subcutaneously with carrageenan (10 μl of 1% solution in saline) into the right paw. Anti-inflammatory properties of external anemonin were studied by applying with various liniment solution of anemonin (0.125, 0.5, 2 mg/ml, 0.5 ml) for 2 h immediately after administration of carrageenan. The rats of control group were treated with the same volume of solvent (25%

2.2.3 Effect of Anemonin on the Injured Skin in Mice

ICR mice were utilized for the studies. The dorsal hair of mice was cut and injured 24 hour before experiment. 25% ethanol (0.5 ml) and the liniment solution of anemonin (0.05, 0.5, 5 mg/ml, 0.5 ml) were coated 4 h a day for 7 days on the area of hairless which was 2×2 cm$^2$ per mice. The skin irritation was evaluated by visual scoring (Table C-3 and C-4) everyday. The mice were continuously observed for 7 days after stopping applying. Application of 25% ethanol and 0.05 mg/ml anemonin did not cause any irritation on injured skin, which began to recover from the forth day of administration and healed up till the seventh day. Application of 0.5 mg/ml anemonin caused a slight erythema after 24 h application, then began to alleviate. The injured skin of application 0.5 mg/ml anemonin also healed up within 7 days. Application of 5 mg/ml anemonin caused a mild to moderate erythema.

TABLE C-3

Visual score criterion for evaluating skin irritation

| Irritation | Score |
|---|---|
| No evidence erythema | 0 |
| Mild erythema | 1 |
| Moderate erythema | 2 |
| Severe erythema | 3 |
| Severe erythema and eachar formation | 4 |

TABLE C-4

Visual score criterion for evaluating skin irritation

| Grade | Score |
|---|---|
| No irritation | <0.5 |
| Mide irritation | <2.09 |
| Moderate irritation | <6.0 |
| Severe irritation | >6.0 |

TABLE C-5

Effect of application of anemonin on the injured skin in mice

| Day | 25% ethanol Irritation Score | Grade | Anemonin 5 mg/ml Irritation Score | Grade | Anemonin 0.5 mg/ml Irritation Score | Grade | Anemonin 0.05 mg/ml Irritation Score | Grade |
|---|---|---|---|---|---|---|---|---|
| | | | Treatment | | | | | |
| 1 | 0 | No | 3.1 | Moderate | 1 | Mild | 0 | No |
| 2 | 0 | No | 3.4 | Moderate | 0.25 | No | 0 | No |
| 3 | 0 | No | 3.3 | Moderate | 0.25 | No | 0 | No |
| 4 | 0 | No | 3.3 | Moderate | 0.25 | No | 0 | No |
| 5 | 0 | No | 3.3 | Moderate | 0.125 | No | 0 | No |
| 6 | 0 | No | 4 | Moderate | 0 | No | 0 | No |
| 7 | 0 | No | 4 | Moderate | 0 | No | 0 | No |
| | | | Observation | | | | | |
| 8 | 0 | No | 4 | Moderate | 0 | No | 0 | No |
| 9 | 0 | No | 4 | Moderate | 0 | No | 0 | No |
| 10 | 0 | No | 3.5 | Moderate | 0 | No | 0 | No |
| 11 | 0 | No | 3 | Moderate | 0 | No | 0 | No |
| 12 | 0 | No | 2.5 | Moderate | 0 | No | 0 | No |
| 13 | 0 | No | 2 | Mild | 0 | No | 0 | No |
| 14 | 0 | No | 2 | Mild | 0 | No | 0 | No |

2.2.4 Cytotoxicity Effect of Anemonin

The cell viability was determined by using 3-(4,5-dimethylthiazol-2-yl)-2,5-Diphenyl-tetrazolium bromide (MTT) assay. In brief, fresh spleen cells were obtained from ICR mice (male, 7-9 weeks old), $5 \times 10^5$ of spleen cells were cultured in 96-well flat plates. The medium was contained various concentrations of anemonin. After incubation for up to 48 h, MTT solution (5 mg/m in saline) was added to the 96 plates and cells were allowed to incubate for 6 h at 37° C. After the medium had been removed 100 μl, the cell and dye crystals were solubilized by adding 100 μl 10% sodium dodecyl sulfate (SDS), and then absorption was measured at 570 nM with a model 550-microplate reader (Bio-Rad). The results showed that anemonin at 1-100 μg/ml exhibited cytotoxic effects in a dose-dependent manner.

TABLE C-6 cytotoxicity effect of anemonin

| | Concentration(ug/ml) | OD value | cytotoxicity |
|---|---|---|---|
| Control | | 0.197 ± 0.003 | |
| Anemonin | 0.001 | 0.196 ± 0.006 | No |
| | 0.01 | 0.193 ± 0.007 | No |
| | 0.1 | 0.200 ± 0.011 | No |
| | 1 | 0.160 ± 0.004*** | Yes |
| | 10 | 0.135 ± 0.003*** | Yes |
| | 100 | 0.118 ± 0.011*** | Yes |

*$P < 0.05$;
**$P < 0.01$;
***$P < 0.001$, compared to control (Student's T-test)

2.2.5 Effects of Anemonin on T- and B-Cell Proliferation

Fresh spleen cells were obtained from ICR mice (male, 7-9 weeks old), $5 \times 10^5$ of spleen cells were cultured in 96-well flat plates with 200 μg/ml of RPMI 1640 media containing 10% FBS, 100 U/ml penicillin and 100 μg/ml streptomyin in a humidified, 37° C., 5% $CO_2$ incubator for 48 hrs. The cultures were either unstimulated, or were stimulated with 5 μg/ml of ConA or 10 μg/ml of LPS to induce T cells or B cells proliferative responses respectively.

The compounds were added in cultures with indicated concentrations to test their bioactivities. Profileration was assessed in terms of uptake of [$^3$H]-thymidine during 6-12 hours pulsing with 20 kBq [$^3$H]-thymidine/well, then the cells were harvested by a Basic 96 harvester, and counted in a 1540 MicroBeta Trilux (PerkinElmer Life Sciences). The results demonstrated that this compound 1-100 μg/ml) significantly inhibited T- and B-cell proliferation (Table C-7 and C-8).

TABLE C-7

Effect of anemonin on murine spleens cells proliferation stimulated with ConA

| | Concentration (μg/ml) | [$^3$H]-TDRincorparation(CPM × $10^{-3}$) |
|---|---|---|
| Control | | 32.4 ± 1.22 |
| Anemonin | 0.001 | 30.1 ± 1.31 |
| | 0.01 | 33.2 ± 2.56 |
| | 0.1 | 30.9 ± 0.78 |
| | 1 | 21.7 ± 0.53** |
| | 10 | 0.03 ± 0.01*** |
| | 100 | 0.02 ± 0.01*** |

**$P < 0.01$;
***$P < 0.001$, compared to control (Student's T-test)

TABLE C-8

Effect of anemonin on murine spleens cells proliferation stimulated with LPS

| | Concentration (μg/ml) | [$^3$H]-TDRincorparation(CPM × $10^{-3}$) |
|---|---|---|
| Control | | 43.5 ± 0.76 |
| Anemonin | 0.001 | 52.0 ± 2.27 |
| | 0.01 | 47.2 ± 3.41 |
| | 0.1 | 47.5 ± 3.60 |
| | 1 | 34.4 ± 2.41* |
| | 10 | 0.11 ± 0.15*** |
| | 100 | 0.17 ± 0.26*** |

**$P < 0.01$;
***$P < 0.001$, compared to control (Student's T-test)

2.2.6 Effects of Anemonin on Cytokine Productions from Splenocytes In Vitro

For splenocyte cytokine production assay, $5 \times 10^6$ cells per well were inoculated into a 24-well tissue culture plate with ConA (5 mg/L) or Sac (1:10000) stimulation. Different concentrations of Anemonin were added in a final volume of 2 ml. Cells were incubated at 37° C., 5% $CO_2$ for 24 h and supernatants were harvested, IFN-γ, IL-10, IL12 (p40) and IL-2 in supernatants were measured by the sandwich enzyme-linked immunosorbent assay (ELISA) as specified by the manufacturer (BD Bioscience pharmingen, US). Concentrations of the cytokine productions were calculated based on standard curves obtained from serial dilutions of murine cytokines (r IFN-γ, rIL-10, rIL12, rIL-2). As shown in Tables C-3 and C-4, high-dose Anemonin (1-100 μg/ml) inhibited all kinds of cytokine release induced by ConA or Sac.

TABLE C-9

Effect of Anemonin on cytokine production stimulated by Sac

| | Concentration (μg/ml) | Sac stimulation | | |
|---|---|---|---|---|
| | | IFN-γ(pg/ml) | IL-10(pg/ml) | IL-12(p40)(pg/ml) |
| Control | | 193 ± 3 | 1327 ± 56 | 499 ± 8 |
| Anemonin | 0.001 | 237 ± 3 | 1242 ± 46 | 501 ± 6 |
| | 0.01 | 230 ± 23 | 1235 ± 19 | 446 ± 0 |
| | 0.1 | 143 ± 0 | 1229 ± 9 | 444 ± 3 |
| | 1 | 95 ± 2 | 749 ± 64 | 293 ± 0 |
| | 10 | 98 ± 7 | 249 ± 0 | 86 ± 6 |
| | 100 | 89 ± 2 | 274 ± 18 | 72 ± 4 |

TABLE C-10

Effect of Anemonin on cytokine production stimulated by ConA

| | Concentration (μg/ml) | ConA stimulation | |
|---|---|---|---|
| | | IFN-γ(pg/ml) | IL-2(pg/ml) |
| Control | | 2890 ± 109 | 475 ± 4 |
| Anemonin | 0.001 | 2405 ± 171 | 482 ± 7 |
| | 0.01 | 2651 ± 120 | 479 ± 5 |
| | 0.1 | 2298 ± 4 | 461 ± 2 |
| | 1 | 508 ± 16 | 190 ± 2 |
| | 10 | 94 ± 0 | 22 ± 1 |
| | 100 | 89 ± 3 | 28 ± 1 |

3 Conclusion 3.1 The model of carrageenan-induced rat paw edema and the model of dimethylbenene-induced mice ear edema are acute inflammatory models. The present results showed that external anemonin reduced paw edema developments in rats in a dose-dependent manner, when given immediately after injection of carrageenan. It also inhibited mice ear edema formation induced by dimethylbenene.

3.2 The anti-inflammatory mechanism of anemonin was discussed in this study. The effects of anemonin ov splenocyte proliferation and cytokine produce were measured. The results showed that anemonin at 1-100 μg/ml can affect the cell viability in a dose-dependent manner.

D. Test of In Vitro Percutaneous Penetration Velocity of Anemonin

Anemonin has significant inflammation resistance and diminishment activities and exhibits particularly favorable curative effect on aseptic inflammation. However, anemonin is relatively stronger irritative and may induce nausea, vomiting and diarrhea, stimulate kidney, consequently cause side effects such as bloody urine and proteinuria. Based on its physical and chemical properties, anemonin is supposed to possess percutaneous penetration ability and could be used externally, whereby avoiding its stimulation to stomach and intestine, reducing toxicity to kidney and restraining bad effect. In the present research, the steady penetration rate of anemonin and ethanol effect on which were examined. This would throw light on exploiting percutaneous anemonin preparation.

Results

Figure 1:
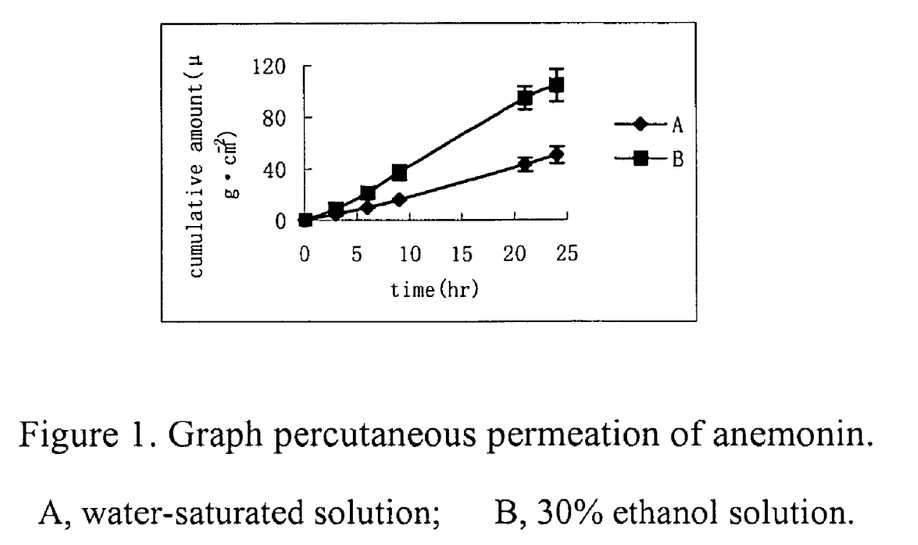
FIG. 1 depicts the percutaneous permeation of anemonin as a plot of permeation amount versus time.

The steady penetration velocity into derma of water saturated anemonin solution examined was 2.28 μg $cm^{-2}$ $h^{-1}$, and was elevated obviously by ethanol. The velocity was doubled by 30% of ethanol (4.65 μg·$cm^2$·$h^{-1}$). Moreover, the ethanol remarkably shortened the time lag of percutaneous permeation (Table D-1 and FIG. 1).

TABLE D-1 parameter of percutaneous permeation of anemonin (X ± SD, n = 3)

| Sample | $Q_{24}$(μg · $cm^{-2}$) | $T_{lag}$(h) | $J_s$ (μg · $cm^{-2}$ · $h^{-1}$) | ER |
|---|---|---|---|---|
| water-saturated solution | 50.49 ± 6.48 | 2.05 ± 0.74 | 2.28 ± 0.39 | 1.0 |
| 30% ethanol solution | 104.45 ± 12.58 | 1.09 ± 0.20 | 4.65 ± 0.47 | 2.0 |

($Q_{24}$: cumulative amount of percutaneous penetration medicament per square centimeter for 24 hours, $T_{lag}$: time lag, $J_s$: steady penetration velocity, ER: increased permeation times)

E. The Experiment of the Anemonin Extract Liquor through Different Extraction Periods and Processes Under different conditions, the natural Chinese herbal medicines which contain the protoanemonin, were turned into Hu San Tie extract liquor (Guanyin Dew) containing Anemonin. The irritability of the extraction by two-month, four-month or six-month hot maceration, as well as three-month, six-month or over eight-month cold maceration were tested.

Skin irritant test with one administration, skin irritant test with several administrations and skin allergic test were carried out for the mentioned 6 extractions separately as follows.

1. Skin Irritant Test with One Administration, the Natural Herb Concentration in the Liquor was up to 300 g/100 ml (High Concentration).

The test was carried out with the two-month, four-month or six-month hot maceration extractions, as well as the three-month, six-month or over eight-month cold maceration extractions by stages separately, so 6 tests were included, the method with every extract liquor was depicted as follow, and the experimental results were showed in Table E-1:

12 rabbits each group, 2.0-2.5 kg, and both sexes. They were randomly divided into four groups: intact skin administration group, injured skin administration group, intact skin control group and injured skin control group. Twenty-four hours before the administration, the hairs on the back of the rabbits were removed with the area of 10×15 cm. The injured skin groups were made by lacerating the skin after removing the hairs. The administration groups were given high concentration of Hu San Tie extract liquor (Guanyin Dew), while the control groups given 25% ethanol, then the animal was bound up and fixed. Twenty-four hours later, the residue on the administration area was removed with warm water. The responses of the administration area were observed after 1, 24, 36 and 72 hours respectively. The irritant reaction and its intensity according to Table E-1 and E-3 were scored. The numbers in Table E-1 was a average score of 3 rabbits in the corresponding group, the numbers with "a" indicated score of the intact skin administration group and the numbers with "b" indicated score of the injured skin control group.

Results: The groups, which were administered with two-month hot maceration or three-month cold maceration liquor, had severe erythema and edema. The groups given four-month hot maceration or six-month cold maceration liquor, had moderate erythema and edema. The groups, which were administered with six-month hot maceration or over eight-month cold maceration liquor, had no erythema or edema, except the injured skin control group. So the irritant reaction with one administration was scored zero and its intensity was estimated as non-irritant (see Table E-1).

2. Skin Irritant Test with Several Administrations. The Natural Herb Concentration in the Liquor was up to 300 g/100 ml (High Concentration).

The irritant test was carried out by stages following the method with the two-month, four-month or six-month hot maceration extractions, as well as the three-month, six-month or over eight-month cold maceration extractions as depicted as follow, so 6 tests were included, the skin was examined pathohistologically as well. The irritant reaction and its intensity according to Table E-2 and E-3 were scored.

12 rabbits each group, 2.0-2.5 kg, and both sexes. They were randomly divided into four groups: intact skin administration group, injured skin administration group, intact skin control group and injured skin control group. The test method and scoring were same with one administration test. An administration was applied each day for seven days. The skin reaction was observed each day during the administration and the another week after administration.

Results: The groups, which were administered with two-month hot maceration or three-month cold maceration extract liquor, had severe erythema, purple edema and scab. The groups given four-month hot maceration or six-month cold maceration liquor, had moderate erythema, edema and some other abnormal skin changes. The groups, which were administered with six-month hot maceration or over eight-month cold maceration liquor, had no erythema, edema or other abnormal skin changes except the injured skin control group. The irritant reaction with several administrations was scored zero and its intensity was estimated as non-irritant. The injured skin scabbed, shed and healed almost at the same time, and there was no obvious difference between the injured skin administration group and control group, which showed that Hu San Tie (Guanyin Dew) did not influenced the process of wound healing. In addition, the pathohistological examination showed that there were no abnormal pathological changes between the administration group and control group (see Table E-2 and E-3).

3. Skin Allergic Test. The Natural Herb Concentration in the Liquor was up to 300 g/100 ml (High Concentration).

Method: Thirty guinea pigs each group, 250-200 g, half male and half female. They were randomly divided into three groups: adminstration group, blank control group and positive control group. Twenty-four hours before the administration, the hairs on the left back of the guinea pigs were removed with the area of 3×3 cm. Then Hu San Tie (Guanyin Dew) was applied on the animals of adminstration group. The animal was bound up and fixed for 6 hours. Another administration was given on the seventh day and fourteenth day after the first one. Blank control group and positive control group was given 25% ethanol and 1% 2,4-dinitrochlorobenzene respectively using the same method. Twenty eight days later after the first administration, the animals in the three groups were removed the hairs on the right back and given Hu San Tie (Guanyin Dew), 25% ethanol and 1% 2,4-dinitrochlorobenzene respectively. Then they were bound up and fixed for six hours. The residue was removed and the skin reactions were observed instantly, 24, 48 and 72 hours later respectively. And we scored the skin allergic reaction and classified its intensity according to Table E-3 and E-4.

The irritant test was carried out by stages following the above method with the two-month, four-month or six-month hot maceration extractions, as well as the three-month, six-month or over eight-month cold maceration extractions.

Results: The skin allergic reaction was scored 4 with administration of two-month hot maceration or three-month cold maceration liquor, scored 3 with administration of four-month hot maceration or six-month cold maceration liquor, and the skin allergic reaction of the adminstration group, the blank control group and the positive control group with administration of six-month hot maceration or over eight-month cold maceration liquor, were scored zero, zero and seven respectively. The allergenic rate of administration group, blank control group and positive control group were 0%, 0% and 100%, and the allergenic intensity were weak, weak and extreme respectively. The results showed that Hu San Tie liquor (Guanyin Dew) according to the present invention could not cause allergic reaction and belonged to non-allergenic substance (see Table E-4 and E-5).

4. Tables

TABLE E-1 skin irritant test with one administration of Hu San Tie liquor (Guanyin Dew) by two, four or six-months hot maceration, as well as the three, six or over eight-months cold maceration.

| Irritant reaction | Standard score | Hot 2 months | Hot 4 months | Hot 6 months | Cold 3 months | Cold 6 months | Cold 8 months |
|---|---|---|---|---|---|---|---|
| Erythema: | | | | | | | |
| without erythema | 0 | | | $0^a$ $0^b$ | | | $0^a$ $0^b$ |
| scarcely observable | 1 | | | | | | |
| Moderate erythema | 2 | | $2^a$ $2^b$ | | | $2^a$ $2^b$ | |
| Severe erythema | 3 | $3^a$ $3^b$ | | | $3^a$ $3^b$ | | |

TABLE E-1-continued skin irritant test with one administration of Hu San Tie liquor (Guanyin Dew) by two, four or six-months hot maceration, as well as the three, six or over eight-months cold maceration.

| Irritant reaction | Standard score | Hot 2 months | Hot 4 months | Hot 6 months | Cold 3 months | Cold 6 months | Cold 8 months |
|---|---|---|---|---|---|---|---|
| Purple erythema and scab | 4 | | | | | | |
| Edema: | | | | | | | |
| Without edema | 0 | | | $0^a$ $0^b$ | | | $0^a$ $0^b$ |
| Hardly observable | 1 | | | | | | |
| Clear apophysis | 2 | | $2^a$ $2^b$ | | | $2^a$ $2^b$ | |
| Apophysis about 1 mm and enlarging | 4 | $4^a$ $4^b$ | | | $4^a$ $4^b$ | | |

TABLE E-2 skin irritant test with several administrations of Hu San Tie liquor (Guanyin Dew) by two, four or six-months hot maceration, as well as three, six or over eight-months cold maceration

| Irritant reaction | Standard score | Hot 2 month | Hot 4 month | Hot 6 month | Cold 3 month | Cold 6 month | Cold 8 month |
|---|---|---|---|---|---|---|---|
| Erythema: | | | | | | | |
| without erythema | 0 | | | $0^a$ $0^b$ | | | $0^a$ $0^b$ |
| scarcely observable | 1 | | | | | | |
| Moderate erythema | 2 | | $2^a$ $2^b$ | | | $2^a$ $2^b$ | |
| Severe erythema | 3 | | | | | | |
| Purple erythema and scab | 4 | $4^a$ $4^b$ | | | $4^a$ $4^b$ | | |
| Edema: | | | | | | | |
| Without edema | 0 | | | $0^a$ $0^b$ | | | $0^a$ $0^b$ |
| Hardly observable | 1 | | | | | | |
| Clear apophysis | 2 | | $2^a$ $2^b$ | | | $2^a$ $2^b$ | |
| Apophysis about 1 mm and enlarging | 4 | $4^a$ $4^b$ | | | $4^a$ $2^b$ | | |

TABLE E-3

The evaluation of skin irritant intensity after giving Hu San Tie liquor (Guanyin Dew) by two, four or six-month hot maceration, as well as three, six or over eight-month cold maceration

| Allergenic rate % | Reaction intensity | Hot 2 month | Hot 4 month | Hot 6 month | Cold 3 month | Cold 6 month | Cold 8 month |
|---|---|---|---|---|---|---|---|
| 0-10 | Weakly allergenic | | | 0-10 | | | 0-10 |
| 20-30 | Slightly allergenic | | | | | | |
| 40-60 | Moderately allergenic | | 40-60 | | | 40-60 | |
| 70-80 | Highly allergenic | 70-80 | | | 70-80 | | |
| 90-100 | Extremely allergenic | | | | | | |

TABLE E-4

The evaluation of skin allergic reaction after giving Hu San Tie liquor (Guanyin Dew) by two, four or six-months hot maceration, as well as three, six or over eight-months cold maceration

| Skin response | Standard score | Hot 2 month | Hot 4 month | Hot 6 month | Cold 3 month | Cold 6 month | Cold 8 month |
|---|---|---|---|---|---|---|---|
| Erythema: | | | | | | | |
| without erythema | 0 | | | 0 | | | 0 |
| Weak erythema | 1 | | | | | | |
| Moderate erythema | 2 | | | | | | |
| Severe erythema | 3 | | 3 | | | 3 | |
| Dropsical erythema | 4 | 4 | | | 4 | | |
| Edema: | | | | | | | |
| Without edema | 0 | | | 0 | | | 0 |
| Weak edema | 1 | | | | | | |
| Moderate edema | 2 | | 2 | | | 2 | |
| Severe edema | 3 | 3 | | | 3 | | |

TABLE E-5

The evaluation of skin allergenic rate after giving Hu San Tie liquor (Guanyin Dew) by two, four or six-month hot maceration, as well as three, six or over eight-month cold maceration

| Allergenic rate % | Reaction intensity | Hot 2 month | Hot 4 month | Hot 6 month | Cold 3 month | Cold 6 month | Cold 8 month |
|---|---|---|---|---|---|---|---|
| 0–10 | Weakly allergenic | | | 0–10 | | | 0–10 |
| 20–30 | Slightly allergenic | | | | | | |
| 40–60 | Moderately allergenic | | 40–60 | | | 40–60 | |
| 70–80 | Highly allergenic | 70–80 | | | 70–80 | | |
| 90–100 | Extremely allergenic | | | | | | |

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

The invention claimed is:

1. A method for treatment of aseptic inflammations and related pain, edema, adhesions and combinations thereof comprising administration to a patient in need thereof a medicament consisting essentially of a therapeutically effective amount of anemonin.

2. The method according to claim 1, wherein the anemonin is a chemical synthetic product.

3. The method according to claim 1, wherein the anemonin originates from an extract of a natural plant containing anemonin or an anemonin precursor or precursors.

4. The method according to claim 3, wherein the natural plant is selected from the group consisting of *Ranunculus* plants, *Ranunculus japonicus* Thunb., *Caltha palustris* L., *Ranunculus sceleratus* L., *Anemone hupehensis* Lem., *Pulsatillia chinensis* (Bge.) Regel, *Anemone raddeana* Regel, *Ranuncuius Chinensis* Regel, *Anemone altaica* Fisch, *Clematis chinensis* osbeck, *Clematis finetiana* Levi. Et Vant., *Clematis hexapetaia* Pall, *Clematis Manshurica* Rupr., *Clematis paniculata, Clematis florida, Clematis lasiandra* Maxim, *Clematis uncinata* champ. ex Benth, *Clematis meyeniana* Walp, *Anemone hupehensis* Lem. var. *japonica* (Thunb.) Bowles et Steam, *Graminaceous* plants, root of *Imperata cylindrica*, ranunculin containing plants, *Ranunculaceae Helleborus, Anemone, Hepatica, Ranunculus, Baractrachium*, and *Aconitum scaposum* var. vaginatum.

5. The method according to claim 3, wherein the anemonin extract is obtained by extracting the natural plant with an organic solvent as an extractant; and wherein the extraction is carried out under sealed conditions.

6. The method according to claim 5, wherein the anemonin extract is further obtained by cold extraction of the natural plant with 30 to 50% strength ethanol at room temperature for 8 months or more.

7. The method according to claim 5, wherein the anemonin extract is further obtained by heating 30 to 50% strength ethanol to boiling, adding the natural plant, heating the ethanol and the natural plant to boiling, and wherein the container containing the ethanol and the natural plant is sealed and stored for 6 months or more.

8. The method according to claim 5, wherein the organic solvent is selected from the group consisting of methanol, ethanol, propandiol, glycerine, chloroform, and mixtures thereof.

9. The method according to claim 1, wherein the medicament is administrated in preparation selected from the group consisting of an oral preparation, a preparation for injection, or a topical preparation.

10. The method according to claim 9, wherein the topical preparation is selected from the group consisting of an ointment, a liquid extract, a plaster, a suppository, a wet towel, a liniment, and a paint; and wherein said preparation is transdermally absorbed.

11. The method according to claim 9, wherein the topical preparation is an ointment comprising an extract of a natural plant and further comprises 95% strength ethanol as a preservative.

12. The method according to claim 10, wherein the topical preparation is provided in a wet towel; and wherein the wet towel is prepared by soaking gauze or non-woven fabrics with a liquor containing anemonin as an active component in an amount of 12.5 mg of anemonin per 25 ml of said liquor.

13. The method according to claim 12, wherein the method further comprises applying the wet towel on the affected or painful site at the rate of one administration per week for 3 weeks, and wherein each administration is applied for 4 to 6 hours.

14. The method according to claim 12, wherein the liquor contains anemonin in an amount of about 12.5 mg of anemonin per 25 ml of the liquor and the gauze or non-woven fabrics are 100 $cm^2$ in size.

15. The method according to claim 14, wherein the method further comprises applying the wet towel on the affected or painful site at the rate of one administration per week for 3 weeks, and wherein each administration is applied for 4 to 6 hours.

16. The method according to claim 1, wherein the aseptic inflammations and related pain are associated with a condition selected from the group consisting of edema, adhesions, cervical spondylosis, lumbar diseases, periarthritis humeroscapularis, tennis elbow, muscular fascia syndrome, rheumatic arthritis, osteoarthritis, aseptic prostatitis, multiple neuritis, neurodermatitis, tenosynovitis, lumbar muscle strain, ischias, painful heel, migraine, stomach ache, cancerous pain, bronchial asthma, and necrosis of the femoral head caused by aseptic inflammations.

* * * * *